United States Patent [19]

Lara et al.

[11] Patent Number: 5,596,267
[45] Date of Patent: Jan. 21, 1997

[54] APPARATUS AND METHOD FOR MEASURING POTENTIALS THROUGH PAVEMENTS FOR BURIED PIPELINE CATHODIC PROTECTION SYSTEMS

[75] Inventors: Pedro F. Lara, Dallas; Mark W. Mateer, Plano, both of Tex.

[73] Assignee: Atlantic Richfield Company, Los Angeles, Calif.

[21] Appl. No.: 361,758

[22] Filed: Dec. 22, 1994

[51] Int. Cl.$^6$ ..................................................... G01R 27/26
[52] U.S. Cl. ........................... 324/71.1; 324/425; 204/402
[58] Field of Search .................................. 324/71.1, 71.2, 324/425; 204/196, 197, 404; 205/724, 727, 730, 734

[56] References Cited

U.S. PATENT DOCUMENTS

| 4,388,168 | 6/1983 | Burkhart | 204/196 |
| 4,806,850 | 2/1989 | Saunmade et al. | 324/71.2 X |
| 5,144,247 | 9/1992 | Speck | 324/71.1 X |
| 5,469,048 | 11/1995 | Donohue | 324/425 X |

OTHER PUBLICATIONS

"Techniques for Cathodic Protection Testing Over Airfield Pavements", Civil and Environmental Engineering Development Office, Tyndall AFB, FL 32403, Apr. 1979.

Primary Examiner—Maura K. Regan
Attorney, Agent, or Firm—Michael E. Martin

[57] ABSTRACT

Fluid transmission pipelines and similar structures which are cathodically protected from electrolytic corrosion and are disposed in urban areas under pavements and other structures which prevent access to the soil for verifying pipe-to-soil potentials are subjected to pipe-to-soil potential measurements using a reference electrode disposed in a container which has a permeable bottom and which is capable of saturating a pavement layer with a brine electrolyte to provide electrical conductivity between the reference electrode and the soil. Validation of electrical conductivity is made by a second reference electrode of a dissimilar metal which is also disposed in a container having a permeable bottom and an electrolyte which permeates the pavement layer and establishes electrical conductivity between the soil and the second reference electrode. Potential measurements between the first and second electrodes validate ion transport between the soil and the first reference electrode. Pipe-to-soil potential measurements are carried out between the reference electrode and a connection to the pipe using a wireless transmission system or using an electrical power grid neutral or ground wire as the conductor between the pipe and the reference electrode. Pipe-to-soil potential measurements may be made without penetrating the pavement and without trailing wires between the point of connection to the pipe and the available point of connection between the reference electrode and the soil.

10 Claims, 4 Drawing Sheets

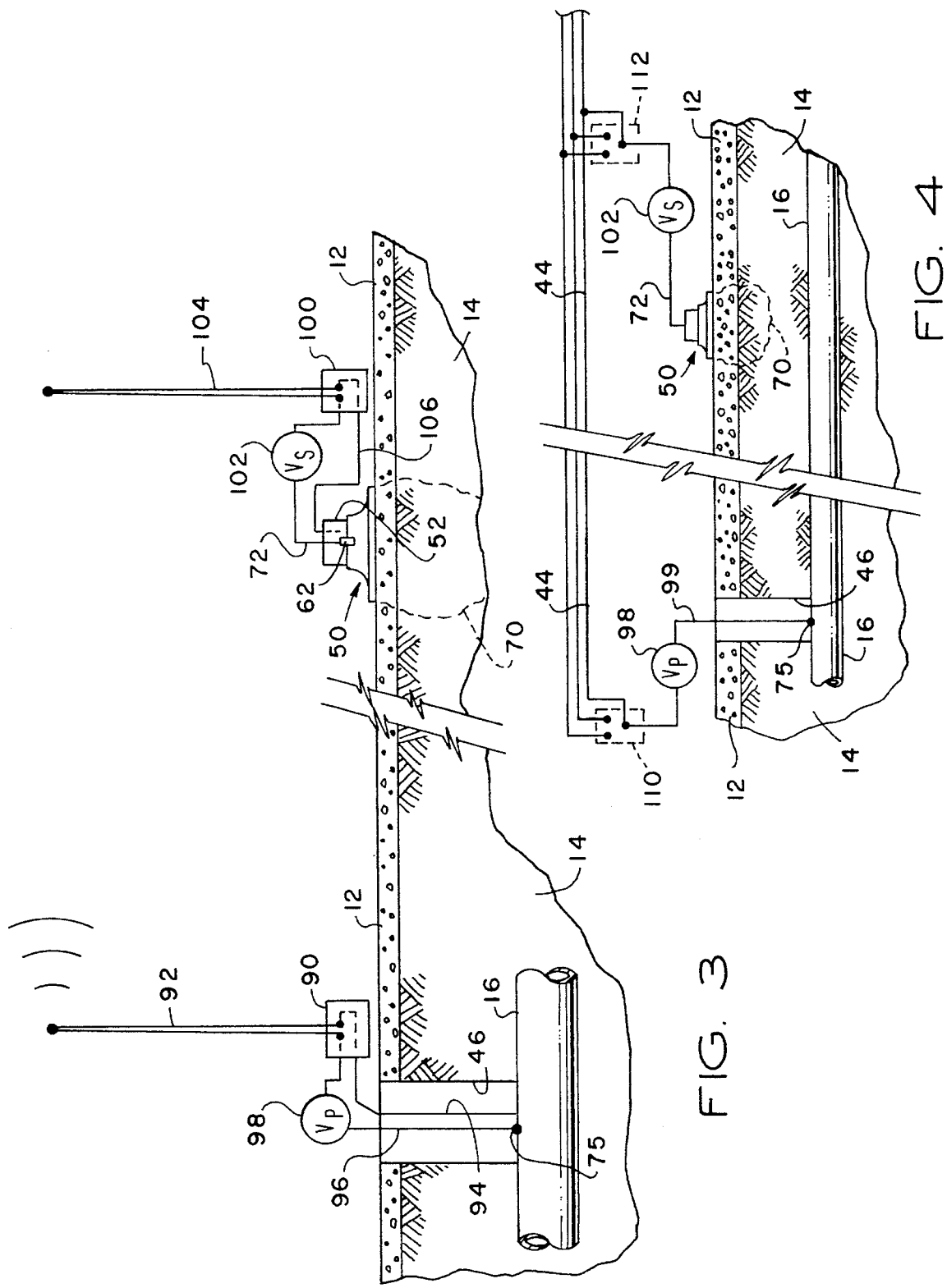

APPARATUS AND METHOD FOR MEASURING POTENTIALS THROUGH PAVEMENTS FOR BURIED PIPELINE CATHODIC PROTECTION SYSTEMS

FIELD OF THE INVENTION

The present invention pertains to apparatus and methods for measuring potentials between buried pipelines and the soil wherein the pipelines are connected to a cathodic protection system and are disposed in urban areas, in particular.

BACKGROUND OF THE INVENTION

Many miles of buried, steel fluid transmission pipeline extend through urban areas where the earth's surface is paved with asphalt or concrete or various structures are disposed over the pipeline. Various types of fluid transmission pipelines and similar buried structures are required to employ cathodic protection systems to avoid corrosion of the buried metal. In this regard, a source of direct current (DC) is applied through the positive source electrode to a ground circuit, which may comprise a mass of buried steel or an abandoned pipeline, for example, and the negative electrode of the source is connected to the pipe or other structure to be protected so that the structure to be protected becomes the cathode in any electrolytic reaction with the surrounding soil and, thus, is not subject to electrolytic corrosion. Pipelines equipped with cathodic protection systems are usually tested from time to time to verify that a correct negative potential exists between the soil and the pipe to assure that the cathodic protection of the pipe is effective. However, pipelines running under urban areas present great difficulty in making the cathodic protection verification measurements.

For example, conventional practice in verifying the correct operation of a pipeline cathodic protection system comprises attaching one lead of a voltmeter to the pipe itself and the other lead to a suitable grounding or reference electrode in contact with the soil in the vicinity of the pipe. In some urban areas, access ducts or manholes are provided in the street or sidewalk pavement for access to the pipeline but access to the soil under the pavement in the vicinity of the selected measurement points for the pipeline is often difficult or impossible to achieve. Moreover, the presence of structures such as buildings, paved roadways and sidewalks, the associated pedestrian and vehicle traffic and the existence of regulatory requirements prohibit forming any type of hole in the pavement to gain access to the soil in the test area. Still further, the stringing of conductor wire between the pipeline access duct or manhole and a point of measurement where the soil is exposed is inconvenient and may be virtually impossible to carry out due to the distances required and the fact that the wire cannot be strung along the roadways or sidewalks in the aforementioned urban setting.

Accordingly, the aforementioned difficulties in testing pipeline cathodic protection systems to verify proper operation, particularly in urban areas, have heretofore made the test procedure unreasonably expensive and subject to delays due to regulatory requirements, and in some cases virtually impossible because of conditions which do not favor providing access to the soil through public and private asphalt or concrete roadways, other paved areas such as parking lots and sidewalks and, of course, through interior floors or walls of private or public structures. However, notwithstanding the difficulty of gaining access to the soil surrounding buried pipelines in such urban settings, the requirements to monitor such pipelines for proper cathodic protection still exist.

Certain types of electrodes or contactors have been developed which are intended to establish electrical contact with the earth through certain types of pavement. However, verification that a suitable conductive path has been established is difficult with such devices and the question remains as to whether or not a correct pipe-to-soil potential measurement can be made or confirmed when the reference electrode is disposed on a pavement surface above the soil in which the reference electrode is intended to be in electrically conductive engagement. Accordingly, there has also been a need to verify that proper electrically conductive engagement is established between the reference electrode and the soil in the vicinity of the pipeline so that measurement of the pipe-to-soil potential can be established. The present invention is directed to solving the above-mentioned problems in measuring the proper operation of cathodic protection systems for buried pipelines and other similar structures which are buried in the soil and for which cathodic protection systems are in use.

SUMMARY OF THE INVENTION

The present invention provides a unique method for measuring electrical potentials between buried pipelines and similar structures and the surrounding soil wherein a cathodic protection system is intended to be in effect to prevent electrolytic corrosion of the pipe or other structure.

In accordance with one important aspect of the invention, a method for measuring pipe-to-soil potentials for buried pipelines and the like, having cathodic protection systems connected thereto, is provided for use in urban areas where paved roadways, sidewalks and other structures prevent direct access to the soil in the vicinity of the pipeline.

In accordance with one embodiment of the invention, pipe-to-soil potentials are measured by connecting a radio transmitter to the pipe by way of a voltmeter and grounding the transmitter antenna to the pipe. A radio signal is transmitted to a receiver which is connected to a voltmeter which is in electrically conductive engagement with the soil and the antenna for the receiver is also electrically grounded to the soil. The pipe-to-soil potential is obtained by calculating the difference between the measured voltage (RMS) of the signal transmitted by the transmitter, minus any attenuation in the transmitted signal, and the voltage (RMS) of the signal received at the receiver antenna and established between the receiver antenna and the soil. In this way the pipe-to-soil potential may be measured without directly interconnecting the pipeline with a reference electrode in electrically conductive engagement with the soil and which electrode may be required to be disposed some distance from a voltmeter and the electrode which is connected to the pipeline. Radio transmission avoids the stringing of long conductor wires in urban areas over roadways and sidewalks, for example.

In accordance with another embodiment of the invention, pipe-to-soil potentials may be determined by utilizing a neutral or ground wire of an electrical power transmission grid extending within the urban area or setting at which pipeline cathodic protection measurements are to be made. Electrical potential between the so-called neutral or ground wire and the pipe may be measured and potential between the ground wire and the soil at a suitable measuring point may be measured. One or the other of these measurements alone may be made.

Still further in accordance with the present invention, the pipe-to-soil potential measurement may be made utilizing electrical ground cables or similar structures in urban areas in the vicinity of power grid substations, for example. Other conductors which may be grounded to a common ground cable may be utilized as a conductor for interconnecting a voltmeter with the pipe and with the soil in the place a measurement is intended to be carried out.

The present invention further provides a unique apparatus and method for establishing electrical conductivity between a reference electrode and soil under a layer of pavement. A unique electrolyte dispensing and holding apparatus, including reference electrode support means, is provided in accordance with the invention for establishing electrical conductivity between a reference electrode and soil under a layer of pavement.

Still further, the present invention provides a unique apparatus and method for validating the establishment of proper electrical conductivity between a reference electrode and soil under a layer of pavement or the like.

Those skilled in the art will further appreciate the above-mentioned advantages and features of the present invention together with other superior aspects thereof upon reading the detailed description which follows in conjunction with the drawing.

BRIEF DESCRIPTION OF THE DRAWING

FIG. 3 is a schematic diagram illustrating one system and method for measuring pipe-to-soil potentials in accordance with the invention;

FIG. 4 is a schematic diagram illustrating another system and method in accordance with the invention for measuring pipe-to-soil potentials;

DESCRIPTION OF PREFERRED EMBODIMENTS

Figure 1:
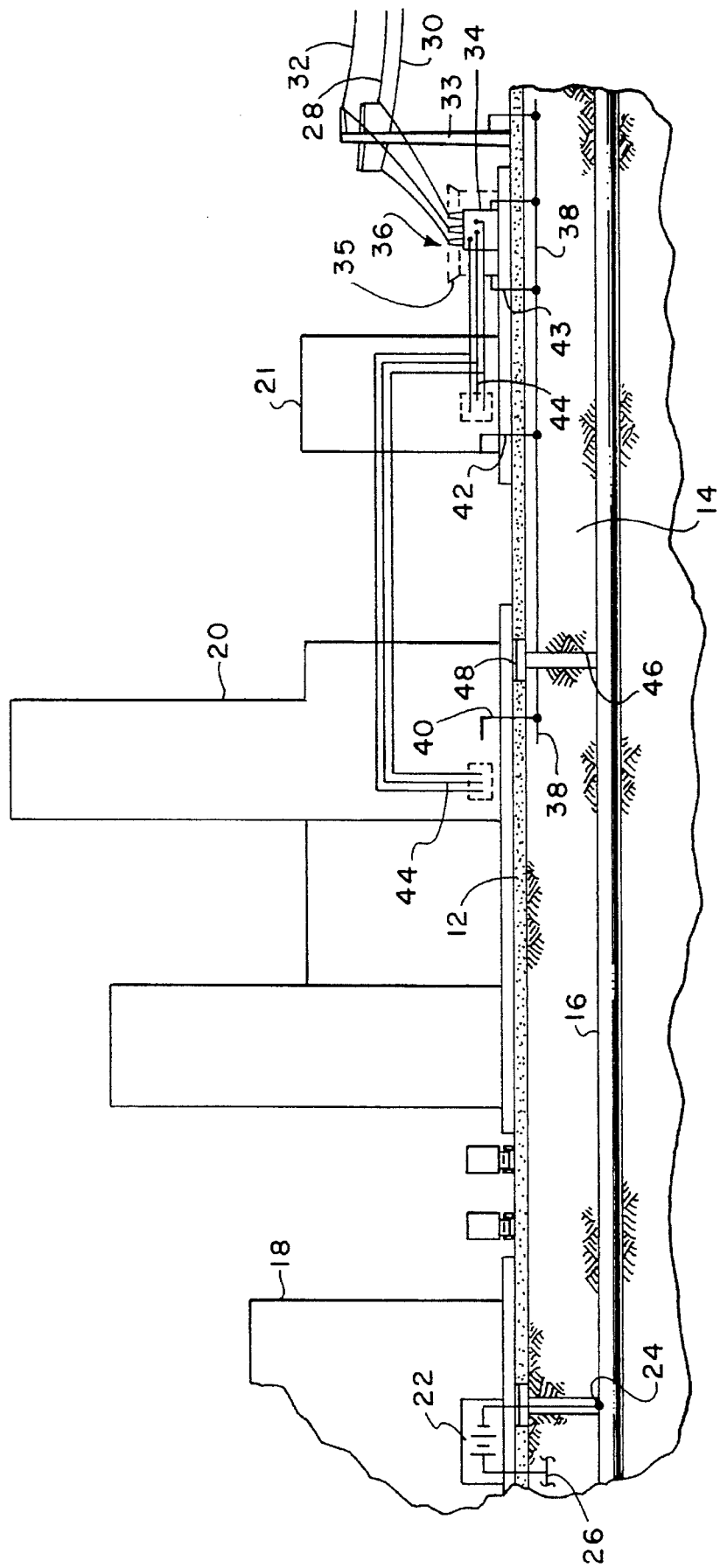
FIG. 1 is a sectioned elevation, in somewhat schematic form, of an urban area in which a buried pipeline is to be measured for proper cathodic protection in accordance with the present invention.

In the description which follows like elements are marked throughout the specification and drawing with the same reference numerals, respectively. The drawing figures are shown in somewhat schematic or generalized form to facilitate understanding the systems and methods of the invention.

Referring to FIG. 1, there is illustrated an urban area or setting, generally designated by the numeral 10, in which one or more layers of asphalt or concrete pavement 12 substantially covers the soil of the underlying earth 14 in which is buried a fluid transmission pipeline 16. Multiple buildings 18, 20 and 21 are also arranged in the urban area 10 and cover the earth 14 substantially within the area in which the effectiveness of a cathodic protection system for the pipeline 16 is to be tested. The pipeline 16 is shown connected to a cathodic protection system including a source 22 of DC current wherein the pipeline 16 is connected to the negative terminal of the source 22 at 24 and the positive terminal of the source 22 is connected to the soil or earth 14 at 26. The connection 26 may include a mass of conductive metal such as a relatively large steel electrode or even an abandoned pipeline, not shown. In any event, the pipeline 16 is a cathode for the circuit which includes the source 22 and the soil 14 as a conductor. In this way, electrolytic corrosion of the pipeline 16 is substantially minimized.

The diagram of FIG. 1 also illustrates a portion of an AC (alternating current) electrical power grid, typical of the type found in essentially all urban areas as well as various rural settings. The power grid includes plural overhead transmission lines 28, 30 and 32, in which transmission line 32 is considered a so-called neutral or ground conductor. The transmission lines 28, 30 and 32 are connected to a suitable transformer 34 located at a substation 36 which is configured to have suitable ground conductor means connected to the transformer as well as substantially all conductive structures at the substation, including, for example, protective metal fencing 35. The aforementioned ground conductor means are connected to a common ground conductor or cable 38 buried in the soil 14. The cable 38 may also extend to certain buildings such as the buildings 20 and 21 wherein the steel frames of the buildings themselves are grounded to the cable 38 through suitable ground conductors 40 and 42, for example. In this way, all structures including a transmission line support tower 33, the transformer 34, the substation protective fence 35, and the steel framework of the buildings 20 and 21 may be suitably grounded. FIG. 1 shows the fence 35 grounded to cable 38 through a conductor 43, for example.

Of course, each of the buildings, 20 and 21 for example, also has a power transmission network suitably connected to the transformer 34, for example, including conductors which correspond to the conductors 28, 30 and 32 and include a neutral or ground wire 44. In other words, a common ground conductor 44 extends from the transformer 34, for example, throughout the urban area 10 to each electrical outlet or the like within the buildings 18, 20, 21 and so on.

FIG. 1 further illustrates a point of access to the pipeline 16 such as an access shaft manhole or manway 46 extending through the pavement layer 12 to the pipeline and being suitably closed at the surface of the pavement layer 12 by a removable cover 48. Such access shafts usually are placed at predetermined but substantially spaced apart locations throughout the urban setting for access to the pipeline 16.

The conventional method for measuring proper electrical potential between the soil and a pipeline, underground tank or other structure, including the pipeline 16, is to connect an electrode to the pipeline and to a suitable voltmeter and then connect a reference electrode to the soil 14 and also to the same voltmeter. Suitable standards exist for the minimum potential which is measurable when a proper connection between the pipeline and the soil is established. For example, certain regulatory requirements require that a measurement of negative 0.85 volts (relative to a copper/copper sulfate reference electrode) be obtained between the soil and the pipeline 16, for example, at predetermined measurement points. However, as previously mentioned, the proper measurement of the requisite potential between the pipe and soil is difficult to obtain in an urban setting such as the urban area 10. Access to the soil 14 under the pavement layer 12 may be difficult if not impossible. A treatise entitled "Techniques for Cathodic Protection Testing Over Airfield Pavements" by B. Husock, U.S. Air Force, Civil and Environmental Engineering Report, CEEDO-TR-78-31, April 1979, describes a procedure for cathodic protection testing wherein airfield runway pavement is drilled to gain access to the pipeline or the soil underneath. This procedure may not be carried out in many areas for various reasons.

Accordingly, there is a need to establish electrical conductivity with the soil 14 in the vicinity of the pipeline 16 at predetermined points to determine if proper potentials exist therebetween. Of course, the electrode connected to the pipeline 16 or the soil may be connected to a voltmeter by a long "trailing wire" so that the soil may be measured at some point where access to such is obtainable. However, stringing a wire over the pavement in an urban setting with heavy pedestrian and vehicle traffic is at least impractical if not virtually impossible to carry out. As previously mentioned, there are also known types of reference electrodes which have been developed for establishing electrical conductivity through pavement layers to the soil underneath. However, these reference electrodes may not be reliable and it is believed that validation of establishment of electrical conductivity between the soil and reference electrodes has not heretofore been carried out.

Figure 2:
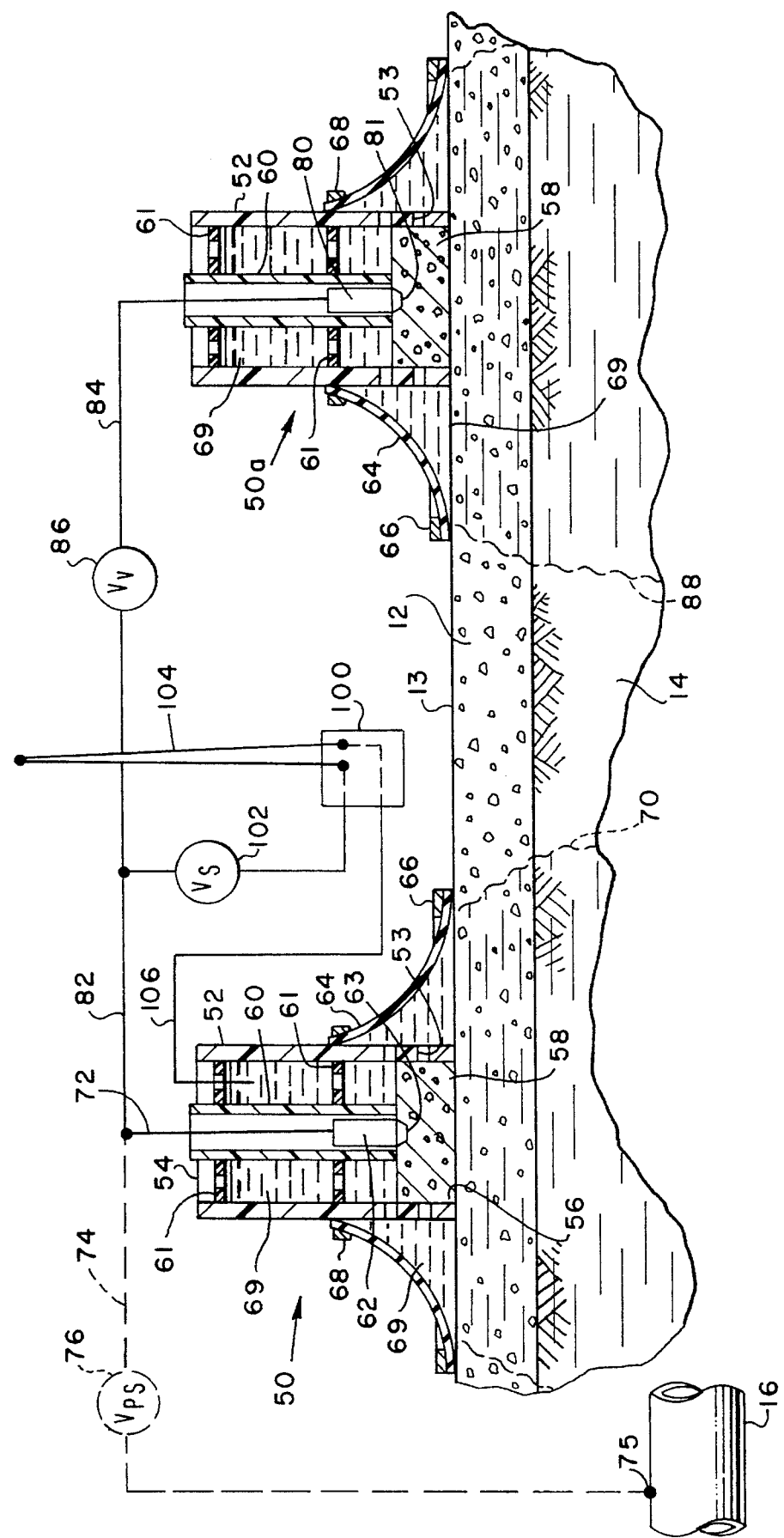
FIG. 2 is a sectioned elevation of an apparatus for establishing electrical conductivity between a reference electrode and soil under a layer of pavement and an apparatus for validating the establishment of such electrical conductivity in accordance with the invention.

The present invention provides a unique apparatus for establishing electrical conductivity between a reference electrode and the soil under a layer of pavement. Referring to FIG. 2, there is shown a portion of the pavement layer 12 overlying the soil 14 and on which pavement a unique apparatus is disposed and generally designated by the numeral 50. The apparatus 50 is characterized by a generally cylindrical container 52 having an open top end 54 and an open bottom end 56. The container 52 is essentially a sleeve or cylinder of approximately 6.0 inches diameter and having about a 0.75 inch wall thickness and preferably formed of nylon or a similar plastic. The container 52 includes a fluid permeable bottom closure characterized by a layer of open cell rubber sponge 58 which is suitably secured in the container adjacent the bottom end 56 such as by an interference fit.

The permeable bottom closure 58 is operable to be in forcible engagement with the surface 13 of the pavement layer 12 and for diffusing a suitable electrolyte through the pavement layer and into the underlying soil 14 in accordance with the invention. An elongated cylindrical sleeve 60 is supported in the container 52 above the bottom closure 58 by spaced apart foraminous webs 61. The sleeve 60 is operable to locate a suitable reference electrode 62 therein and in electrically conductive engagement with the closure 58. The electrode 62 may be of a type commercially available and used as a ground or soil engaging electrode for cathodic protection measurement systems. One source of the electrode 62 is M. C. Miller Company, Ringwood, N.J. The electrode 62 may be a copper/copper-sulfate type, silver/silver chloride or a calomel/potassium-chloride type, for example.

Figure 6:
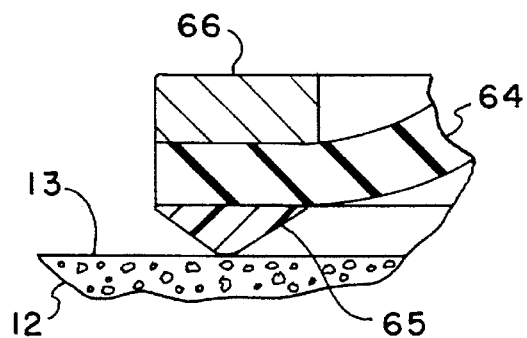
FIG. 6 is a detail section view showing a seal arrangement for the apparatus illustrated in FIG. 2.

The apparatus 50 is further characterized by a somewhat frusto-conical, depending, circumferential skirt 64 disposed around the container 52 and engageable with the surface 13 of the pavement layer 12. The skirt 64 may be formed of a suitable elastomeric material, such as silicone rubber, for example. As shown in FIG. 6, a unique triangular cross section seal ring 65 is secured to the peripheral edge of the skirt 64 for sealing engagement with the pavement surface 13. The seal ring 65 may be formed of flexible closed cell neoprene. The skirt 64 and seal ring 65 are held in secure, substantially fluid-tight engagement with the surface 13 by a cylindrical ring weight 66. The skirt 64 is also secured to the container 52 by a suitable band clamp 68 in fluid tight engagement with the outer surface of the container. The ring 66 is preferably made of steel or cast iron and is of sufficient weight to hold the skirt 64 in fluid-tight engagement with the surface 13. The diameter of the skirt 64 at its point of contact with the surface 13 may be about 18.0 inches, which, preferably, is also the outer diameter of the ring 66. A steel ring having a 2.0 inch width and a 0.25 inch thickness would weigh approximately 12.5 pounds and may be sufficient to hold the skirt 64/seal ring 65 in fluid-tight engagement with the pavement surface 13. More or thicker ring weights may be required.

As further shown in FIG. 2, the container 52 includes plural sidewall ports 53 opening to the exterior of the container below the point of engagement of the skirt 64 with the container at the band clamp 68. A suitable electrolyte 69, such as sea water or a brine solution having approximately thirty-five parts per thousand of sodium chloride or potassium chloride dissolved in water, may be poured into the container 52 to flow through the ports 53 and soak into the pavement layer 12 substantially within the circular area defined by the skirt 64. The electrolyte will also permeate through the bottom closure 58 of the container 52 and eventually develop a plume 70 of saturated pavement and soil 14 beneath the apparatus 50.

With a thorough soaking of the pavement layer 12 within the envelope defined by the skirt 64 the apparatus 50 will establish sufficient electrical conductivity between the electrode 62 and the soil 14 to make suitable potential measurements between the electrode and the soil. The apparatus 50 advantageously enhances the establishment of electrical conductivity between the electrode 62 and the soil under a layer of pavement such as the pavement 12. Accordingly, if it is possible to interconnect the pipe 16, as shown in phantom in FIG. 2, with the electrode 62 by way of a conductor 72, 74, an electrode 75 and a suitable voltmeter 76, potential measurements between the pipe 16 and the soil 14 may be made directly. However, as mentioned previously, such an arrangement is often unlikely to be available.

A problem related to providing electrical conductivity between the electrode 62 and the soil 14 using the apparatus 50 pertains to validation that suitable conductivity has been established. In this regard, the present invention contemplates the provision of a second apparatus 50a, see FIG. 2, in contact with the surface 13 of the pavement 12 and preferably disposed within a distance of about five to ten feet from the apparatus 50. The apparatus 50a illustrated in FIG. 2 is essentially identical to the apparatus 50 except that a second reference electrode 80 is disposed in the sleeve 60 and engaged with the permeable bottom closure 58. The electrodes 62 and 80 are interconnected by suitable conductors 82 and 84 and a voltmeter 86.

If electrolyte 69 in the container 52 of the apparatus 50a has suitably penetrated the pavement layer 12 to establish a plume 88 of saturated soil 14, and electrical conductivity is established between the electrode 80 and the soil 14 directly below the second apparatus 50, a predetermined voltage may be measured at the voltmeter 86. In order to establish a voltage measurable at the voltmeter 86, the electrode 80 is of a dissimilar metal with respect to the electrode 62. For example, the electrode 80 may be of a type commercially available from the above-mentioned vendor of the electrode 62 and be of a silver/silver chloride type used in measuring electrical potentials between pipelines and soils, for example. If ion transport is occurring between the soil 14 and the electrode 62 and also between soil 14 and the electrode 80 and the electrodes are of copper/copper sulfate and silver/silver chloride, respectively, a precise measurement of 94.0 millivolts will be read at the voltmeter 86. If the electrode 62 is a calomel/potassium chloride electrode and the electrode 80 is a silver/silver chloride electrode a precise measurement of 19.0 millivolts may be observed at the voltmeter 86 if uninhibited ion transport is occurring between the soil 14 and the respective electrodes. If either of the electrodes 62 or 80 is not in suitable electrically conductive communication with the soil 14 a reduced voltage in the range of less than 1.0 millivolts will be observed. Accordingly, unique apparatus for establishing electrical conductivity between a reference electrode and soil under a pavement layer, such as the pavement 12, and for validating such establishment of electrical conductivity is provided in accordance with the invention.

In establishing electrical conductivity between the soil 14 and the electrode 62, for example, the apparatus 50 is placed on the pavement layer 12 with the permeable closure 58 in contact with the surface 13 and the skirt 64 in fluid tight engagement with the surface 13 in the position shown in FIG. 2. A suitable electrolyte such as sea water or brine is poured into the container 52 to a level above the lower contact surface 63 of the electrode 62 and maintained at that level for a period of time to assure that the electrolyte permeates the pavement layer 12 into the soil 14 below the pavement. The electrode 62 may then have its conductor 72 suitably connected to a measurement system in accordance with the invention including connecting the conductor 72 directly to a voltmeter 76 by way of a conductor 74 and which voltmeter is in conductive engagement with the pipeline 16.

Alternatively, an apparatus 50a is placed five to ten feet away from the apparatus 50 and a suitable electrode, such as the electrode 80, is placed in the guide sleeve 60. The apparatus 50a is also filled with the aforementioned electrolyte solution and the solution is allowed to permeate through the pavement layer 12 into the soil 14. A suitable quantity of electrolyte is maintained in the container 52 of the second apparatus 50a so that the level of electrolyte is above the contact surface 81 of the electrode 80. The electrodes 62 and 80 are then interconnected by way of voltmeter 86 and measurements taken to determine if suitable ion transport is occurring between the soil 14 and the respective electrodes. The voltmeters 76 and 86 are preferably a high impedance type (impedance exceeding two hundred terra ohms, for example) and may be of a type commercially available under the designation Electrometer from Keithley Instruments, Inc.

Once validation of electrical conductivity between the electrode 62 and the soil 14, for example, has been established the apparatus 50a and its electrode 80 may be disconnected from the apparatus 50 or the system illustrated in FIG. 2 may be left intact. In any event, an improved method of measuring the potential between a pipeline 16 and soil 14 will now be described in conjunction with FIG. 3. Referring to FIG. 3, there is illustrated a system including a radio transmitter 90 having a suitable transmission antenna 92 operably connected thereto. The antenna 92 is suitably grounded to the pipeline 16 by way of a conductor 94 extending within the access shaft 46. The transmitter 90 is also connected to the pipe 16 by way of a conductor 96 having a suitable voltmeter 98 interposed therein and which may be of the aforementioned type. As also shown in FIG. 3, a radio receiver 100 is connected to the apparatus 50 and its electrode 62 by way of a circuit including a conductor 72 and a voltmeter 102. A receiving antenna 104 is operably connected to the radio receiver 100 and to a grounding conductor 106 which is suitably disposed in electrically conductive engagement with electrolyte 69 in the container 52, see FIG. 2 also. In this way, the receiver antenna 104 is effectively grounded to the soil 14 through the apparatus 50. The transmitter 90 and its antenna 92 may be operated to transmit a signal having a known magnetic intensity and with predetermined attenuation characteristics. The attenuation characteristics of the antenna 92 with respect to the antenna 104 may be predetermined based on the distance between the antennas, atmospheric conditions and other conditions which may interfere with signal intensity or amplitude.

By connecting one of the input terminals of the antennas 90 and 104 to the respective voltmeters 98 an 102 and grounding the antennas, respectively, to the pipe 16 and the soil 14, the pipe-to-soil potential between the pipe 16 and the soil 14 at the apparatus 50 may be determined by measuring the RMS (root mean square) field potential ($V_p$) relative to the pipe at the access shaft 46 during transmission of a signal from antenna 92 by radio transmitter 90. The RMS field potential of the signal received at antenna 104 relative to the soil is measured by the voltmeter 102. This is voltage, $V_s$. The potential loss, $V_a$, due to attenuation of the transmitted signal is determined from the aforementioned attenuation characteristics. The pipe-to-soil potential, $V_{ps}$, is then determined from the equation:

$$V_{ps}=V_p-(V_a+V_s)$$

Of course, in order to measure the pipe-to-soil potential, $V_{ps}$, accurately, the signal attenuation voltage, $V_a$, must be limited to a relatively small fraction of the transmitted signal, $V_p$. It is contemplated that distances between the transmitter antenna 92 and the receiver antenna 104 may range from five hundred feet to fifteen hundred feet while incurring minimal attenuation losses. Such an arrangement may well be suitable for measuring pipe-to-soil potentials of a cathodic protection system for pipelines wherein access to the soil in the vicinity of the pipeline at selected points of measurement is not practical.

The present invention contemplates an alternate method for measuring pipe-to-soil potentials in pipeline cathodic protection systems wherein access to the soil is prevented but an apparatus 50 may be employed to establish electrical conductivity between a reference electrode 62 and the soil 14. Referring to FIG. 4, for example, the pipe 16 may be connected to a reference conductor 99 which is in circuit with a voltmeter 98 and is connected to the neutral or ground conductor 44 of the aforementioned electrical transmission and distribution grid or system. Since the conductor 44 is a common conductor throughout the system, it may serve as a conductor between the pipe 16 and the soil 14 by way of the apparatus 50 and the associated reference electrode 62. The voltmeter 98 and/or 102 may be employed to measure the pipe-to-soil potential between the pipeline 16 and the soil 14 by way of the conductors 99, 44 and 72.

Accordingly, by connecting the conductor 99 and the voltmeter 98 to the transmission grid neutral or ground conductor 44 at a suitable outlet or connection point 110, for example, and by also connecting the apparatus 50 by way of its conductor 72 and voltmeter 102 to the same neutral or ground conductor 44 at an outlet 112 at a location remote from the access shaft 46 pipe-to-soil voltage potential may be measured at the location of the apparatus 50. Any difference in the measured voltages at the voltmeters 98 and 102 due to currents carried by the conductor 44 may be noted and subtracted. The location of the apparatus 50 may, of course, be changed so that pipe-to-soil potentials may be measured at selected points along the pipeline 16.

Figure 5:
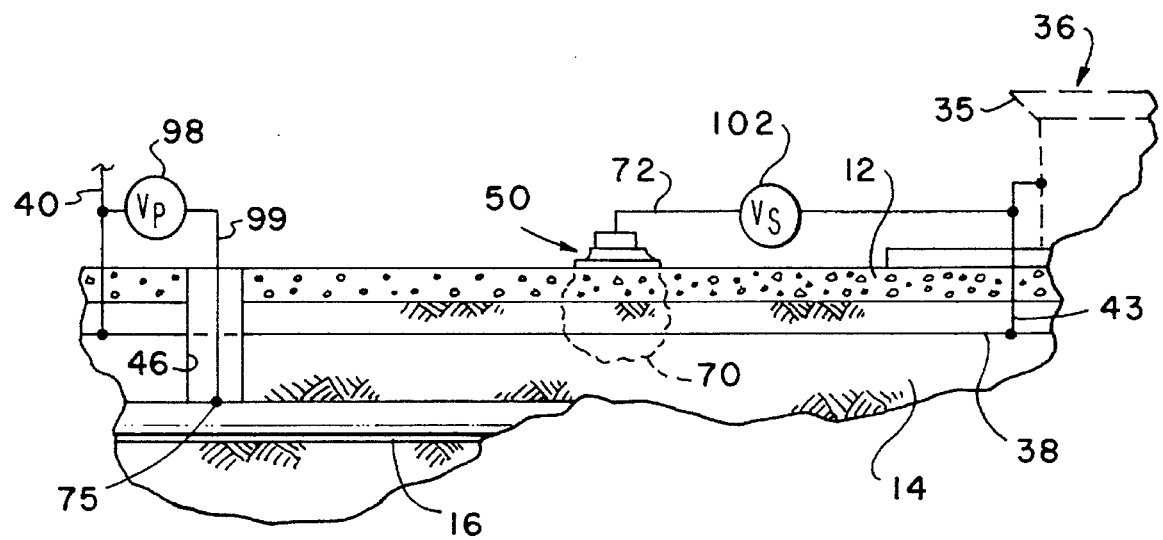
FIG. 5 is a schematic diagram of still another system and method for measuring pipe-to-soil potentials in accordance with the invention.

Referring to FIG. 5, a modification of the method and arrangement described above in conjunction with FIG. 4 is illustrated wherein the pipeline 16 is connected to a ground conductor 38 which may be available in certain locales and, in particular, in the vicinity of an electrical distribution substation 36, for example. FIG. 5 illustrates, by way of example, an arrangement wherein a conductor 99 is connected to pipeline 16 at the access shaft 46 and to a ground conductor 40 such as might be available at the building 20, FIG. 1. Since this ground conductor 40 is connected to the common ground conductor 38 which also grounds the fence 35 disposed around substation 36, then, if the apparatus 50 is disposed in the vicinity of the connection between the fence 35 and the ground conductor 38, as indicated by conductor 43, pipe-to-soil voltage potential measurements may be obtained using the common conductor 38, 40, 43. As with the system illustrated in FIG. 4, only one of the voltmeters 98 or 102 may be required to establish the pipe-to-soil potential with the circuit illustrated in FIG. 5.

Improved methods and systems for making pipe-to-soil voltage potential measurements in conjunction with pipeline and other buried structure cathodic protection systems have been described hereinabove. However, those skilled in the art will recognize that various substitutions and modifications may be made to the invention without departing from the scope and spirit of the appended claims.

What is claimed is:

1. A method for making pipe-to-soil potential measurements for verifying the operability of a cathodic protection system for a fluid transmission pipeline disposed in soil under a layer of pavement, comprising the steps of:

saturating at a first location a layer of pavement above said soil which is to be placed in electrically conductive engagement with a first reference electrode with a first quantity of an electrolyte which penetrates said pavement and into said soil to establish an ion transport path between said soil and said first reference electrode;

placing said first reference electrode in electrically conductive engagement with said soil through said electrolyte; and measuring a potential signal between said first reference electrode and a second reference electrode connected to said pipe.

2. The method set forth in claim 1 wherein:

the step of saturating said pavement with said electrolyte is carried out by positioning a container onto said layer of pavement at said first location, said container holding a quantity of said electrolyte and having a bottom closure with sufficient permeability to allow said electrolyte to penetrate said bottom closure and said pavement, and means for supporting said first reference electrode in conductive engagement with said electrolyte to establish ion transport between said soil under said pavement and said first reference electrode.

3. The method set forth in claim 2 wherein:

said container includes a depending skirt defining a chamber for holding a quantity of said electrolyte for penetration through said layer of pavement around said container.

4. The method set forth in claim 1 including the step of:

providing said electrolyte as one of sea water and brine.

5. The method set forth in claim 1 including the steps of:

saturating said pavement with a second quantity of electrolyte which penetrates said pavement and into said soil at a second location which is spaced from said first location where said pavement is penetrated by said first quantity of electrolyte, placing a third reference electrode in electrically conductive engagement between said soil and said second quantity of electrolyte at said second location; and measuring a potential between said first reference electrode and said third reference electrode to verify that said first reference electrode has established electrical conductivity with said soil.

6. The method set forth in claim 1 including the step of:

connecting said pipe to a conductor which is connected to said first reference electrode and having a measurement instrument interposed therein for measuring the potential between said pipe and said soil through said first reference electrode.

7. The method set forth in claim 1 including the steps of:

connecting said pipe in electrically conductive engagement with a neutral conductor of an electrical power transmission system;

placing said first reference electrode in electrically conductive engagement with said neutral conductor; and measuring the potential between said pipe and said soil through said neutral conductor.

8. The method set forth in claim 1 including the steps of:

providing a radio transmitter including a transmitting antenna which is grounded to said pipe;

providing a radio receiver including a receiving antenna which is grounded to said soil through said electrolyte;

transmitting an electromagnetic signal from said transmitter to said receiver;

measuring the electromagnetic field potential of said transmitted signal relative to said pipe;

measuring the electromagnetic field potential of a signal received by said receiving antenna relative to said soil; and determining the pipe-to-soil potential from the difference between the measured field potential signals relative to said pipe and the measured field potential signal relative to said soil.

9. The method set forth in claim 8 including the step of:

determining the field potential signal loss from attenuation between the transmitting antenna and receiving antenna and adding said attenuation signal loss to the field potential signal measured relative to said soil at said receiving antenna.

10. The method set forth in claim 1 including the step of:

locating a ground conductor;

operably connecting said ground conductor to said pipe through said second reference electrode at a predetermined location and operably connecting said ground conductor to said first reference electrode; and measuring the potential between said pipe and said soil through said reference electrodes and said ground conductor.

* * * * *